United States Patent
Dal Farra et al.

(10) Patent No.: US 9,028,889 B2
(45) Date of Patent: May 12, 2015

(54) USE OF COMPOSITION COMPRISING A PEPTIDIC FAVA BEAN EXTRACT FOR THE STIMULATION OF HAIR GROWTH

(75) Inventors: Claude Dal Farra, Kerhonkson, NY (US); Nouha Domloge, Valbonne (FR); Jean-Marie Botto, Valbonne (FR)

(73) Assignee: ISP Investments Inc., Wilmington, DE (US)

( * ) Notice: Subject to any disclaimer, the term of this patent is extended or adjusted under 35 U.S.C. 154(b) by 34 days.

(21) Appl. No.: 13/812,947

(22) PCT Filed: Jul. 18, 2011

(86) PCT No.: PCT/IB2011/002441
§ 371 (c)(1),
(2), (4) Date: Apr. 2, 2013

(87) PCT Pub. No.: WO2012/014081
PCT Pub. Date: Feb. 2, 2012

(65) Prior Publication Data
US 2013/0189381 A1    Jul. 25, 2013

(30) Foreign Application Priority Data
Jul. 29, 2010 (FR) ...................... 10 03188

(51) Int. Cl.
| A61K 36/48 | (2006.01) |
| A61K 36/899 | (2006.01) |
| A61K 8/97 | (2006.01) |
| A61Q 7/00 | (2006.01) |

(52) U.S. Cl.
CPC .... *A61K 8/97* (2013.01); *A61Q 7/00* (2013.01)

(58) Field of Classification Search
CPC ..... A61K 36/48; A61K 36/899; A61K 35/00; A61K 6/645
USPC .............. 424/757, 750, 70.1, 70.14
See application file for complete search history.

(56) References Cited

U.S. PATENT DOCUMENTS

| 5,183,817 | A * | 2/1993 | Bazzano .................... 514/256 |
| 6,509,042 | B1 | 1/2003 | Koren et al. |
| 2004/0241129 | A1* | 12/2004 | Perrier et al. ............ 424/70.14 |
| 2005/0112078 | A1 | 5/2005 | Boddupalli et al. |
| 2012/0220523 | A1 | 8/2012 | Dal Farra et al. |

FOREIGN PATENT DOCUMENTS

| FR | 2650950 | 2/1991 |
| FR | 2949781 | 3/2001 |
| FR | 2904543 | 2/2008 |
| FR | 2925326 | 6/2009 |
| FR | 2925331 | 6/2009 |
| FR | 2951948 | 5/2011 |
| GB | 2261818 | 6/1993 |
| JP | 6100423 | 4/1994 |
| JP | 2002114646 A * | 4/2002 |
| WO | 2007/046636 | 4/2007 |
| WO | 2007/108632 | 9/2007 |

OTHER PUBLICATIONS

Abdullah, F. et al., "Alopecia: Botanical Approaches in Review," *Journal of Drugs in Dermatology*, vol. 9, No. 5, pp. 537-541 (May 2010).
Acuti, G. et al., "Effects of field bean (*Vicia faba* L. var minor) dietary supplementation on plasma thyroid hormones, insulin, insulin-like growth factor-1 concentrations and mohair characteristics in growing Angora goat kids," *Journal of Animal Physiology and Animal Nutrition*, 93, pp. 456-466 (2009).
Arouete, J., "Vieillissement des cheveux," *J. Méd. Esth. et Chir. Derm.*, vol. XXX, pp. 165-167 (Sep. 2003).
Bernard, B.A., "La vie révélée du follicule de cheveu humain," *Medecine/Sciences*, No. 2, vol. 22, pp. 138-143 (Feb. 2006).
Geyfman, M. et al., "Clock genes, hair growth and aging," *Aging*, vol. 2, No. 2, pp. 1-7 (Feb. 2009).
Geyfman, M. et al., "Clock genes, hair growth and aging," *Aging*, vol. 2, No. 3, pp. 122-128 (Mar. 2010).
Kondratov, R.V. et al., "Early aging and age-related pathologies in mice deficient in BMAL1, the core component of the circadian clock," *Genes & Development*, 20, pp. 1868-1873 (2006).
Lin, K.K. et al., "Circadian Clock Genes Contribute to the Regulation of Hair Follicle Cycling," *PLoS Genetics*, vol. 5, No. 7, pp. 1-14 (Jul. 2009).
PCT, International Search Report and Written Opinion, International Application No. PCT/IB2011/002441 (mailed Feb. 15, 2013).
Acuti, G. et al., "Effects of field bean (*Vicia faba* L. var minor) dietary supplementation of plasma thyroid hormones, insulin, insulin-like growth factor-1 concentrations and mohair characteristics in growing Angora goat kids," *Journal of Animal Physiology and Animal Nutrition*, vol. 93, No. 4, pp. 456-466 (Aug. 2009).
Osborne, T.B., *The Vegetable Proteins, Second Edition*, published by Longmans, Green and Co., London, 1924, Chapter IX, pp. 68-88.

* cited by examiner

*Primary Examiner* — Chris R Tate
*Assistant Examiner* — Deborah Davis
(74) *Attorney, Agent, or Firm* — Thompson Hine LLP

(57) ABSTRACT

The present invention relates to the use of a composition comprising at least one peptidic fava bean extract as an active agent capable of limiting hair loss, and/or stimulating its growth. Moreover, the composition is intended, on one hand, to modulate the Clock, Per1 and Bmal1 genes in the dermal papilla cells, and, on the other hand, to restore the circadian rhythm and resynchronize the biological clock of said cells. Finally, the present invention relates to several methods of non-therapeutic cosmetic treatment using said composition.

14 Claims, No Drawings

USE OF COMPOSITION COMPRISING A PEPTIDIC FAVA BEAN EXTRACT FOR THE STIMULATION OF HAIR GROWTH

The present invention relates to the field of cosmetic and pharmaceutical compositions applied to hair. The present invention relates to a composition comprising at least one peptidic fava bean extract to reduce hair loss and/or stimulate hair growth, as well as several non-therapeutic cosmetic treatment methods using said composition.

Human hair is a keratin appendage, just as body hair, eyelashes, eyebrows or nails. It plays a physiological role in protecting the scalp, but above all, and since a long time in the history of man, a social role. Hair can be of various types, long, short, straight, curly . . . but it always obeys a cyclic law. Indeed, the 100,000 to 150,000 hair follicles, which form "normal" hair, are all cyclically, asynchronously and stochastically renewed from a pool of adult follicular stem cells.

Both in men and women, it may be observed that it is normal to lose 100 to 150 hairs a day. Hair falls out and renews itself But hair losses far in excess of 150 hairs, or its failure to be renewed by another follicle (very fine, or rarefied hair), is referred to as hair loss, also known as alopecia. By alopecia is meant total or partial, permanent or transitory loss of scalp hair or body hair, due mainly to age, genetic factors or in response to a local or general condition. There are different types of alopecia according to the origin of the disorder:

alopecia related to age, or old age;

androgenic alopecia (often hereditary) is the most common: it is evidenced by a decrease in the volume of hair or baldness, affecting 70% of men (but it also affecting women);

acute alopecia: this may be related to chemotherapy treatments, stress, strong dietary deficiencies, iron deficiency, hormonal disorders, acute irradiation;

localized alopecia: which can be caused by skin problems (tumors, burns, pelade), radiotherapy or parasites (ringworm, lichen);

congenital alopecia;

alopecia areata, which appears to be of auto-immune origin (cell-mediated mechanism) which is characterized by a "patchy" impairment of varying extent, and in one or more locations. This form of pelade can affect the entire head, in which case it is referred to as alopecia totalis, and sometimes the entire body, in which case it is referred to as Alopecia Universalis (in this case, there is a total loss of body hair and scalp hair from the entire body).

Various cosmetic and/or medical treatments have been developed in recent years in order to treat the different types of alopecia as well as possible. For example, many treatments have been developed to treat androgenic alopecia, since it is a type of alopecia that affects many people, especially men. This type of alopecia is due to an excessive sensitivity to male hormones or androgens, which is itself due to hereditary factors. Under the influence of an enzyme, 5-alpha-reductase, testosterone is converted to dihydrotestosterone or DHT, which stimulates the sebaceous glands. This thus results in a permanent seborrhea, which leads to gradual obstruction of the hair follicle and asphyxia of the bulb, resulting in the abrupt discontinuation of the anagen phase.

However alopecia is mostly related to age and does not necessarily require this type of treatment, which also is associated with side effects. In addition, a significant component of androgenic alopecia is itself due to age. This is why another approach was investigated, that of the growth cycle of hair. Indeed, the hair follicle is a cutaneous appendage with its own autonomous hormonal control, its own cycle, and a complex and stable structure (Bernard B. A.; Médecine/Sciences 2006; 22: 138-43). The hair cycle can be broken down into 3 phases: anagen, catagen and telogen. The anagen phase, or growth phase of the hair, lasts between 3 and 7 years (depending on age, gender and area of the scalp). This phase is followed by a rest, so-called catagen, phase and lasts approximately 3 weeks. Whereas apoptotic processes take place during the catagen phase, causing hair loss, the next phase, referred to as the telogen phase, will enable a new bulb to form from a hair germ which will initiate the next cycle (Arouete J., J. Med. Esth. And Chir. Derm., September 2003, 119, 165-167). This telogen phase, in turn, lasts approximately 3 months. Thus, in "normal" hair, about 85% of follicles are in their growth phase, 2% are in their rest phase, and little more than 10% are in their hair-loss phase.

It has recently been shown that the circadian cycle regulatory genes, such as the CLOCK gene, have an expression correlated with the growth cycle of hair with, in particular, an increased expression during the transition from the telogen phase to the anagen phase (Geyfinan M. et al. Aging, Vol. 2, No. 2, 2009). The circadian clock is controlled by a negative regulatory loop involving a set of genes, in particular the genes PER-1 (Period), CLOCK (Circadian Locomotor Output Cycles Kaput) and Bmal1 (Brain and Muscle tRNA-like Protein). It has been shown that circadian genes that are overexpressed in the transition between the telogen phase and the beginning of the anagen phase, are all the target genes of the CLOCK/Bmal1 pair, thus including the PERs, Rev-DBD and Erba genes.

In this respect, the Applicant has identified the properties of a particular fava bean extract as an anti hair-loss agent, which is specific in that the fava bean extract is a peptidic extract.

Until now fava bean extracts were incorporated into cosmetic compositions for skin treatment (patent FR 2925331). Other types of fava bean extracts have been incorporated into compositions for the treatment of scars caused by viral infections (U.S. Pat. No. 6,509,042). Japanese patent JP6100423, in turn, describes a composition comprising a fava bean extract and minoxidil to prevent hair whitening. However, so far, no document has described the use of a peptidic fava bean extract to reduce the loss of hair and stimulate its growth.

Thus, the first object of the present invention relates to the use of a composition comprising at least one peptidic fava bean extract as an active agent to reduce the loss of hair and/or stimulate its growth.

A second object of the present invention relates to the use of a composition comprising at least said extract as an active agent to modulate the clock, Per1 and Bmal1 genes in the dermal papilla cells.

A third object of the present invention is the use of said extract for the manufacture of a pharmaceutical composition intended to reduce the loss of hair and/or stimulate its growth in cases of hair loss resulting from a medical condition.

Other objects of the present invention relate to methods of non-therapeutic cosmetic treatment intended to reduce the loss of hair and/or stimulate its growth, resynchronize the biological clock of dermal papilla cells, and finally, strengthen the hair follicle and protect it from external aggressions.

Human keratin fibers to which the invention applies include, in particular, hair, eyebrows, eyelashes, beard and mustache hair, pubic hair and nails. More specifically, the invention applies to scalp hair and/or eyelashes.

Thus, the present invention relates to the use of a composition comprising at least one peptidic fava bean extract as an active agent to reduce the loss of hair and/or stimulate its growth.

By "peptidic extract" is meant a hydrolyzate comprising a mixture of compounds represented mainly by peptides or oligopeptides. According to the invention, the terms "peptidic hydrolyzate", "extract", "solubilized extract" or "active agent" will be used equivalently.

By "active agent capable of reducing the loss of hair and/or stimulating its growth" is meant any peptidic fava bean extract, which is capable of stimulating the hair follicle, stimulating proliferation in the dermal papilla cells, stimulating the expression of proliferation markers such as Ki67, as well as the expression of proteins such as the K14 and K15 keratins.

The extract according to the invention can be used to stimulate hair growth in cases of age-related hair loss due to malfunctions of the growth cycle of hair Indeed, the link between the circadian cycle dysfunction, in particular a Bmal1 deficiency, was demonstrated several years ago (Kondratov et al., Genes Dev., May. 2006, 15; 20 (14): 1868-73). It has also been shown that the expression of the Clock gene decreased with age in the cells of the dermal papilla. Yet it is these cells that have the proliferative potential in the hair follicle. Thus, the fava bean extract of the invention can stimulate the expression of the Ki67 protein and K15 and K14 keratins to strengthen the hair follicle. The extract has demonstrated its effect on the various aforementioned markers (cf. examples). Indeed, there is an increase in the expression of these markers when a composition comprising at least said extract is applied to the dermal papilla cells of hair follicles in a culture. The consequence of these overexpressions translates into reduced hair loss, increased strength of hair, and subsequently, stimulation of its growth.

A second object of the invention relates to the use of at least one peptidic fava bean extract of the invention as an active agent capable of modulating the Clock, Per1 and Bmal1 genes in the dermal papilla cells. By "modulating the Clock, Per1 and Bmal1 genes" is meant being capable of increasing or decreasing their activity, either by increasing or decreasing their protein synthesis (by direct or indirect modulation of gene expression) or by other biological processes such as (de)stabilization of these proteins or (de)stabilization of messenger RNA transcripts. Thus, the peptidic fava bean extract can restore the circadian rhythm and resynchronize the biological clock of dermal papilla cells.

According to an advantageous embodiment of the invention, the extract is a peptidic hydrolyzate resulting from the hydrolysis of the proteins of *Vicia faba* L. fava beans. The peptidic hydrolyzate consists of a mixture of compounds predominantly represented by peptides. The term "peptide" refers to a sequence of two or more amino acids linked by peptide bonds or modified peptide bonds; whereas the term "polypeptide" designates a larger peptide. The use of peptidic hydrolyzates, in particular low molecular weight peptidic hydrolyzates, has many advantages in cosmetics. In addition to generating compounds of peptidic nature that did not already exist in the starting protein mixture, hydrolysis and purification make it possible to obtain mixtures that are more stable, more easily standardizable, and causing no allergic reactions related to dermato-cosmetics.

Extraction Protocol

The active ingredient of the invention may be obtained by extraction of proteins of plant origin, followed by a controlled hydrolysis, which releases biologically active peptidic fragments.

Numerous proteins found in plants are likely to contain biologically active peptide fragments in their structure. Managed hydrolysis can generate these peptidic fragments. In order to practice the invention, it is possible, but not necessary, either to firstly extract the proteins concerned, and then hydrolyze them, or to firstly perform the hydrolysis on a crude extract and thereafter purify the peptide fragments. It is also possible to use certain hydrolyzed extracts without purification of their peptidic fragments corresponding to the biologically active peptides according to the invention, whilst nevertheless ascertaining the presence of such fragments using appropriate analytical means.

To perform the extraction, it is possible to use the whole plant, or a specific part of the plant (leaves, seeds, etc.).

More particularly, according to the invention, plant seeds of the Fabaceae family (legumes), of the species *Vicia faba* L., or fava beans, are used. The term "fava bean" also designates the seed which, consumed fresh or dry, is one of the most anciently cultivated legumes.

Preferably, the active ingredient of the invention is a peptidic hydrolyzate and results from the hydrolysis of the proteins of fava seeds (*Vicia faba* L.).

Any method of extraction or purification known to one skilled in the art can be used to prepare the hydrolyzate of the invention.

In a first step, the plant is crushed using a plant grinder. The resulting powder can subsequently be "de-lipidated" using a conventional organic solvent (such as an alcohol, hexane or acetone).

Plant proteins are thereafter extracted using the conventional modified method (Osborne, 1924); the crushed plant is suspended in an alkaline solution containing an insoluble polyvinylpolypyrrolidone (PVPP) adsorbent (0.01-20%); indeed, it has been observed that this facilitates the subsequent hydrolysis and purification operations. In particular, the concentration of phenol-like substances, interacting with proteins, is significantly reduced.

The soluble fraction, which contains the proteins and carbohydrates, is collected after centrifugation and filtering steps. This crude solution is then hydrolyzed under controlled conditions to generate soluble peptides. According to the invention, hydrolysis is carried out chemically and/or advantageously with proteolytic enzymes. This may include the use of endoproteases of plant origin (papain, bromelain, ficin) and microorganisms (*Aspergillus, Rhizopus, Bacillus*, etc.). This crude form of hydrolyzate is a first form of the active ingredient of the invention.

For the same reasons as given above, that is, for the removal of polyphenol substances, an amount of PVPP is added to the reaction medium in this controlled hydrolysis step.

Following the filtering step, which eliminates the enzymes, the obtained filtrate (solution) is a first form of the active agent of the invention.

This is followed by a dilution phase. Thus, the extract is solubilized in one or more physiologically acceptable solvents such as water, glycerol, ethanol, propylene glycol, butylene glycol, dipropylene glycol, ethoxylated or propoxylated diglycols, cyclic polyols, or any mixture of these solvents. This dilution step is followed by sterilization to obtain a peptidic extract characterized by a content of compounds of peptidic nature, of 1 to 4 g/l.

The hydrolyzate obtained at this stage can be further purified by ultrafiltration in order to select the low molecular weight fractions, preferably less than 6 kDa. Thus, at least 70%, preferably at least 85%, of the peptidic compounds present in the extract are peptides with a size smaller than 6 kDa. The purification is advantageously carried out by consecutive ultrafiltration steps through filters with decreasing porosity, or using a method of the chromatographic type.

Thus, according to an advantageous embodiment of the invention, the peptidic extract has a pH in the range between 4 and 7, preferably in the range between 4 and 5, a dry extract titrating between 2 and 5 g/l and most preferably between 3 and 4 g/l, a content of peptidic compounds in the range between 1 and 4 g/l, preferably between 1.5 and 3.5 g/l, and a sugar content between 0.5 and 1 g/l.

According to a second embodiment of the invention, the solubilized extract may be encapsulated or placed in a cosmetic or pharmaceutical vector such as liposomes or any other microcapsule used in the cosmetics field, or adsorbed on powdered organic polymers, mineral substrates such as talcs and bentonites, and more generally, solubilized in, or attached to, any physiologically acceptable carrier.

Thus, the solubilized extract is used in the compositions of the invention at a concentration of between 0.001% and 5%, preferably at a concentration of between 0.01% and 1%, with respect to the total weight of the final composition.

Preferably, the composition of the invention is in a form suitable for topical application.

The composition according to the invention may in particular consist of a composition for hair care, including a shampoo, a conditioner, a styling lotion, a hair treating lotion for pre- or post-aggressive treatment, a hair styling cream or gel, a restructuring hair lotion, a foam mask treatment, etc.

In particular, the composition may be in the form of a cream, an oil-in-water, water-in-oil emulsion or multiple emulsions of the oil-in-water-in-oil or water-in-oil-in-water type, a suspension, an aqueous gel, or aqueous, alcoholic, or oily solutions. The composition may be more or less fluid and be in the form of a white or colored cream, an ointment, a milk, a lotion, a serum, a foam, a biphase, as well as in the form of an aerosol.

Finally, the composition may comprise any additive commonly used in the intended field of application as well as the additives necessary for their formulation, such as co-solvents (ethanol, glycerol, benzyl alcohol, humectant, . . . ), thickeners, diluents, emulsifiers, antioxidants, hair-dyes, sunscreens, pigments, fillers, preservatives, perfumes, odor absorbers, essential oils, trace elements, essential fatty acids, surfactants, film-forming polymers, chemical or mineral filters, moisturizing agents or thermal waters etc. Examples include water soluble polymers of the naturally occurring polymer type, such as polysaccharides or polypeptides, cellulose derivatives of the methylcellulose or hydroxypropylcellulose type, or synthetic polymers, poloxamers, carbomers, PVA or PVP, and in particular the polymers sold by the ISP company.

In all cases, those skilled in the art will ensure that these additives and their proportions are selected so as not to affect the advantageous properties of the composition of the invention. These additives may, for example, correspond to 0.01 to 20% of the total weight of the composition. When the composition of the invention is an emulsion, the fatty phase may represent from 5 to 80% by weight, preferably 5 to 50% with respect to the total weight of the composition. Emulsifiers and co-emulsifiers used in the composition are selected from those conventionally used in the field. For example, they can be used in a proportion ranging from 0.3 to 30% by weight relative to the total weight of the composition.

Furthermore, the composition of the invention can additionally comprise at least one compound enhancing the hair's health.

Preferably, the composition of the invention further includes vitamins, other peptidic plant extracts, esters of nicotinic acid, trace elements, anti-inflammatory agents, retinoic acid or its derivatives, retinol, inhibitors of 5α-reductase or compounds of peptidic nature derived by chemical synthesis. Vitamin examples include vitamins A, E, B5, B6, C, H, or PP, and trace element examples include zinc, copper, magnesium, as well as silicon.

In a more particular embodiment, the composition of the invention comprises, in addition to the peptidic fava bean hydrolyzate:

at least one cytochrome c activator compound, and/or;

at least one moisturizing compound, such as an aquaporin activating compound and/or;

at least one sirtuin activating compound and/or;

at least one compound, such as collagen, which increases the production of matrix proteins and/or;

at least one compound modulating HSPs and/or;

at least one compound which increases cellular energy and/or;

at least one compound which modulates the pigmentation of hair and/or;

at least one compound which enhances resistance to external aggressions, such as a transglutaminase or HMG-CoA reductase activating compound.

Said aforementioned compounds, can be naturally occurring, such as peptidic hydrolyzates of plants, as well as those of synthetic origin, such as compounds of peptidic nature.

A particular embodiment of the invention relates to the use of a composition which comprises, in addition to the peptidic fava bean hydrolyzate, a peptidic corn hydrolyzate, which constitutes a compound which improve hair's health. Trials have shown the positive effect of this combination of extracts on the proliferation of human dermal papilla cells.

Preferably, the composition of this particular embodiment of the invention comprises between 10 and 90% of a peptidic fava bean extract, and between 10 and 90% of a corn (*Zea mays* L.) hydrolyzate. Preferably, the composition comprises 50% of each extract, respectively.

According to this particular embodiment of the invention, the corn extract can be obtained by any method familiar to those skilled in the art or preferably by one of the methods described in patent applications FR 2 951 948, FR 2 949 781 or FR 2 904 543 or granted patent FR 2 925 326.

According to this particular embodiment of the invention the corn extract and the fava bean extract can be obtained separately and then incorporated into the composition, or can also be produced simultaneously in one and the same hydrolyzate, this single hydrolyzate being subsequently incorporated into the composition.

Because of its particular activities, the extract of the invention can be used as a medicine. Thus, the extract can be used for the manufacture of a pharmaceutical composition intended to reduce hair loss and/or stimulate its growth in cases of hair loss resulting from a medical condition. Indeed, the extract can be incorporated into a pharmaceutical composition to slow the loss of hair or to stimulate its growth in cases of alopecia areata or alopecia caused by skin conditions such as burns or parasites.

A fourth object of the present invention relates to a method of non-therapeutic cosmetic treatment for reducing the loss of hair and/or stimulating its growth, characterized in that a composition according to the invention is applied daily to the area of the scalp to be treated.

Another object of the present invention relates to a non-therapeutic cosmetic treatment designed to resynchronize the circadian clock of the dermal papilla cells, by daily application to the scalp area to be treated of a composition as described above. Resynchronization of said cells involves, inter alia, a modulation of the amount of Clock, Per1 and Bmal1 in said cells.

Finally, a last object of the present invention relates to a method of non-therapeutic cosmetic treatment for strengthening the hair follicle and protecting it from external aggressions, by applying a composition of the invention as a pretreatment before exposure to the sun, to chemicals or heat sources, such as dyes, hair straightening, permanent waves, as well as brushings. Indeed, due to its action on the hair's structure (in particular, keratin K14), the peptidic fava bean extract helps to protect the hair follicle, in particular when it is exposed to aggressive treatments.

Other advantages and features of the invention will become more apparent from the following description of illustrative and non-limiting examples.

EXAMPLE 1

Preparation of a Peptidic Hydrolvzate of Fava Seeds (*Vicia faba* L.)

The seeds of fava beans (*Vicia faba* L.) are dissolved in 10 volumes of water in the presence of 2% Polyclar® 10 (polyvinylpyrrolidone—PVPP—insoluble). The mixture is adjusted to a pH between 6 and 8 with a 1 M aqueous sodium hydroxide solution. Precipitation in an acid medium is then performed. The pellet is redissolved, and after pH adjustment, 2% papain is added to the reaction medium. Hydrolysis is obtained after stirring for 2 hours at 55° C. This is followed by enzyme inactivation by heating the solution at 80° C. for 2 hours. After centrifugation, the supernatant aqueous solution corresponding to a crude fava bean hydrolyzate is recovered.

The method of purification of the crude fava bean hydrolyzate begins with consecutive filtrations using Seitz Orion filter plates with decreasing porosities (down to 0.2 μm) to obtain a light yellow, bright and clear solution, designated hydrolyzate 1.

At this stage, the fava bean hydrolyzate 1 is characterized by a dry extract titrating from 40 to 50 g/kg, a protein content of 20 to 30 g/l and a sugar content of 3 to 5 g/l.

The proteinic nature of hydrolyzate 1 is revealed following electrophoresis analysis on a polyacrylamide gel of NuPAGE® Bis-Tris Pre-cast (Invitrogen). The fava bean protein hydrolyzate is heated to 70° C. for 10 minutes under denaturing reducing conditions in a sample preparation buffer NuPAGE® LDS. A solution of NuPAGE® Antioxidant is added to the inner vessel (cathode) so that the reduced proteins do not re-oxidize during electrophoresis. Protein migration is carried out in the migration buffer NuPAGE® MES using the SeeBlue Plus2 standard as a molecular weight marker. Protein staining is performed using Coomassie Blue R-250®. Under these conditions, it is observed that the obtained peptides have a molecular weight of less than 10 kDa.

Hydrolyzate 1 is then purified in order to retain only those peptides having a molecular weight of less than 6 kDa, using tangential flow filtration. For this purpose, hydrolyzate 1 is pumped under pressure through a Pellicon® carrier equipped with a Pellicon® 2 Biomax, 5 kDa cassette. At the end of the purification, a bright and clear peptidic hydrolyzate is obtained. A dilution phase is then carried out to obtain a peptidic hydrolyzate characterized by a protein content of 1.5 to 3.5 g/l.

This diluted peptidic hydrolyzate is then analyzed by high-pressure liquid chromatography (HPLC) using an HP1100 apparatus controlled by the ChemStation software. The column used during the elution of hydrolyzate 2 is a Nucleosil® 300-5 C4 MPN (125×4 min), for the chromatography of proteins with molecular weights of 0.2 to 25 kDa (according to an appropriate gradient of solvents). Under these chromatographic conditions, several peptide fractions have been isolated. These various fractions are then analyzed by mass spectrometry in order to identify their molecular peaks.

The amino acid composition of the active ingredient of the invention has also been determined. This is done after acid hydrolysis and identification by means of high-pressure liquid chromatography with a PICT (phenyl isothiocyanate) pre-bypass.

An example of amino acid composition of the hydrolyzate is given in the following table (in %):

| Amino acids | % |
|---|---|
| Alanine | 4.8 |
| Aspartic Acid | 12.8 |
| Arginine | 10.6 |
| Glutamic Acid | 20.7 |
| Glycine | 4.8 |
| Histidine | 2.6 |
| Isoleucine | 4.8 |
| Leucine | 8.5 |
| Lysine | 7.4 |
| Phenylalanine | 5.3 |
| Proline | 4.8 |
| Serine | 5.8 |
| Threonine | 4.2 |
| Tyrosine | 4.8 |
| Valine | 5.8 |
| Tryptophan | 5.3 |

EXAMPLE 2

Action of the Peptidic Fava Bean Extract on Follicles Maintained in in vitro Culture Cultures of Scalp Bbiopsies and Inclusion of Cuttings Skin biopsies (from facelifts) with hair are grown in the same way as skin explants. Six-mm biopsies are performed using biopsy punches and are cultured on inserts in a WILLIAM E. medium in the presence of Primocine (Invivogen), 10 μg/ml insulin, 10 ng/ml hydrocortisone and 2 mmol/L L-glutamine.

The skin explants are placed in 6-well plates and are either treated or not treated by placing 20 μl of 0.5% or 1% extract (depending on the experiment) diluted in PBS, in contact with the biopsies, and the culture is performed for 48 hours (or several days depending on the experiment). At the end of the experiment, the explants can be coated in either paraffin or OCT, followed with freezing depending on the type of marker used.

Paraffin Coating:

The biopsies are placed into cassettes and fixed in 10% formalin for 2 hours in an automated apparatus (VIP). Subsequently, the biopsies are dehydrated in a series of alcohol baths (with increasing concentrations and durations), followed by 2 xylene baths, and finally embedded in paraffin. The total duration of this series of operations is approximately twelve hours. The thus coated biopsies are thereafter oriented, and are then cut to 4 μm by means of a microtome.

Embedding in OCT (Optimum Cutting Temperature):

The cuts are made in OCT (optimum cutting temperature) and quickly cooled in a bath of liquid nitrogen. The thus solidified blocks are then cut with a cryotome, such that 6 μm cuts are made. The sections are collected on poly-lysinated observation slides.

2.1 Immunostaining of Keratin K15, Keratin K14, and Ki67

For keratin K14 staining, paraffin sections are used. For that purpose, the sections are deparaffinized and rehydrated prior to the addition of the antibody. A series of xylene baths followed by a series of alcohol baths (with decreasing concentrations and durations) and rinsing in water and then PBS, are carried out for this purpose. Following microwave removal of the mask, the deparaffinized sections are rinsed with PBS for 2 minutes, then coated, and each cutting is incubated in 100 µl of 5% BSA for 30 minutes. Thereafter, 100 µl of anti-K14 primary antibody (Abcam, Mouse monoclonal) diluted to 1/50 is added and placed for at least 60 minutes in a humid chamber with stirring. After rinsing with PBS for 30 minutes, 100 µl of secondary antibody diluted to 1/1000 (Invitrogen, Alexa Fluoro 488 anti-Rabbit) and fluorescence-stained, is added and left for 1 hr with stirring in darkness in a humid chamber. These staining operations are performed for 48 hrs on both treated or untreated biopsies with the peptidic fava bean extract diluted to 1%. The slides are then rinsed in PBS, and mounted between a slide and coverslip using Fluromount G.

For keratin K15 and Ki67 staining, frozen sections are used. For that purpose, the sections are dried in an oven at 37° C. for 30 minutes, then fixed with an acetone bath. After rinsing in PBS for 5 minutes, 100 µl of an anti-K15 primary antibody (Abcam, mouse monoclonal) diluted to 1/50 is added. For staining with the Ki67 protein, 100 µl of anti-Ki67 primary antibody (Novocastra, rabbit polyclonal) diluted to 1/100 is added. After stirring for 60 minutes and immersion in a PBS bath, 100 µl of fluorescence-stained secondary antibody diluted to 1/1000 (Invitrogen, Alexa Fluoro 488 anti-Rabbit) is added and left for 1 hour in darkness under stirring in a humid chamber. After rinsing with PBS, 100 µl of 0.3 nM DAPI is added for 5 minutes with stirring in darkness in a humid chamber. Finally, the slides are rinsed in PBS, and mounted between a slide and coverslip using Fluromount G. The fluorescence intensity is quantified by image analysis using the Image-Pro Analyzer software version 5.

Results

In the case of the proliferation marker Ki67, a significant increase of this marker may be observed in biopsies treated with the peptidic fava bean extract used at 1%.

In the case of K14 and K15 keratins, their expression is also increased. Using fluorescence quantification software, an increase of about 32.6% in keratin K15, and 30.9% in hair follicles of biopsies treated with the active extract relative to untreated biopsies.

Conclusions

It is known that keratin K15 is involved in the early stages of differentiation of keratinocytes in hair follicles and that Ki67 is a marker of cell proliferation. Therefore, it can be concluded that the extract according to the invention was instrumental in activating the renewal and proliferation of cells forming the hair follicle. The increase in keratin K14, in turn, demonstrates the role of the fava bean extract on hair structure, which reinforces hair structure, in particular the cohesion of the ORS.

2.2 Immunostaining of the Clock, Per1 and Bmal1 Proteins

In order to carry out staining with the Clock, Per1 and Bmal1 proteins, frozen sections are used. The sections are prepared as described above, and the primary antibodies are applied. For Clock protein staining, 100 µl of anti-Clock primary antibody (Abcam, rabbit polyclonal) diluted to 1/250 is added. For by the Per1 protein staining, 100 µl of anti-Per1 primary antibody (CosmoBio Co., rabbit polyclonal) diluted to 1/100 is added. Finally, for Bmal1 protein staining, 100 µl of anti-Bmal1 primary antibody (Clinisciences, rabbit polyclonal) diluted to 1/250 is added. In each case, after stirring for 60 minutes and a bath of PBS, 100 µl of fluorescence-stained secondary antibody diluted to 1/1000 (Invitrogen, Alexa Fluoro 488 anti-Rabbit) is added and left for 1 hr in darkness with stirring in a humid chamber. After rinsing with PBS, 100 µl of 0.3 nM DAPI is added for 5 minutes with stirring in darkness in a humid chamber. Finally, the slides are rinsed in PBS, and mounted between a slide and coverslip with Fluromount G.

Results

It may be observed that the staining levels of the Clock, Per1 and Bmal1 proteins are maintained at the same values in the hair follicle cells whether or not a treatment with the active ingredient at 1% has been performed. There has been no increase in the expression of these proteins in the hair follicle cells. These results are consistent with the literature and confirm that the follicles in question are in the anagen phase, that is, the hair's vital phase. It can be concluded that the fava bean extract according to the invention maintains the hair follicle cells in the anagen phase, that is in the active phase.

EXAMPLE 3

Action of the Peptidic Fava Bean Extract on Human Dermal Papilla Cells (HDPC)

Human dermal papilla cells (HDPC) are maintained in a culture in order to achieve immunostaining with the circadian rhythm markers, that is, the Clock, Per1 and Bmal1 proteins. HDPC cells were chosen since it is from these cells that the growth of the hair follicle takes place. The cells are cultured in the presence or absence of the peptidic fava bean extract diluted to 0.5 or 1% for 48 hours. After the cells have been washed with PBS, fixed with cold methanol and then rinsed with PBS, the cells are permeabilized with 0.2% Triton X-100 for 15 minutes under stirring. After rinsing with PBS, the primary antibodies are applied. For staining with the Clock protein, 150 µl of an anti-Clock primary antibody (Abcam, rabbit polyclonal) diluted to 1/250 is added. For staining with the Per1 protein, 150 µl of an anti-Per1 primary antibody (CosmoBio Co., rabbit polyclonal) diluted to 1/100 is added. Finally, for staining with the Bmal1 protein, 100 µl of an anti-Bmal1 primary antibody (Clinisciences, rabbit polyclonal) diluted to 1/250 is added. In each case, after stirring for 60 minutes and rinsing with several PBS baths, 150 µl of a fluorescence-stained secondary antibody diluted to 1/1000 (Invitrogen, Alexa Fluoro 488 anti-Rabbit) is added and left for 1 hour in darkness under stirring in a humid chamber. Finally, the slides are rinsed in PBS, and mounted between a slide and coverslip with Fluromount G. The fluorescence intensity is quantified by image analysis using the Image-Pro Analyzer software version 5.

Results:

It is found that the fava bean extract has increased the expression the Clock protein in the nuclei of the HDPC cells with respect to the cells not treated with the extract. Quantitatively, this increase is approximately 19.1% with the extract used at 0.5%, and 30.7% with the extract used at 1%. This shows that the effect of the fava bean extract is dose-dependent.

The expression of the Bmal1 protein is also increased through the peptidic fava bean extract with respect to untreated HDPC cells. The increased staining of the Bmal1 protein is mainly located around the nucleus. This increase is 21.2% with the extract used at 0.5%, and 48.2% with the extract used at 1% (dose-dependent effect).

The same result is found for the Per1 protein in HDPC cells with respect to untreated cells using the peptidic active ingredient. The increase in Per1 protein is found mainly in the vicinity of the nucleus, but also occurs in the cytoplasm. The observed increase is 33.4% with the extract used at 0.5%, and 41.5% with the extract used at 1% (dose-dependent effect).

In addition, Ki67 staining was performed under the same experimental conditions, in the presence or not of the active ingredient at 0.5 or 1%. An increase in staining by the Ki67 protein in the nucleus is then observed with respect to untreated cells. The increase is 10.8% with the active ingredient used at 0.5%, and 56.2% with the active ingredient used at 1%. This increase in Ki67 staining demonstrates a greater proliferation of dermal papilla cells.

Conclusions:

The different staining operations carried out in the dermal papilla cells showed that the fava bean extract of the invention has increased the expression of the major proteins involved in the circadian rhythm. In addition, the extract helped increase the expression of the Ki67 protein, a protein involved in the cell cycle and present only in proliferating cells.

EXAMPLE 4

Action of the Peptidic Fava Bean Extract on Follicle Growth

Measurements of Follicle Lengthening

Biopsies of skin from facelifts are shaved, and then cultured in a suitable medium (Wiliam E. medium) in the presence or absence of the active peptidic extract at a concentration of 0.5% under condition 1, and 1% under condition 2. In the absence of the active ingredient, the follicles are cultured in PBS. The biopsies are maintained in culture for 17 days, and the treatment with the active ingredient is applied every day, once a day. Photographs are taken with the Vivacam (a small camera fitted to the VivaScope) at time zero. Measurements of the lengthening of the hair shaft are carried out on days 7, 10, 14 and 17.

The photographs taken at the different time points are then reprocessed using the "Image Pro Analyzer" software, which allows the size (in μm) of each hair shaft to be measured separately. The overall lengthening of the treated and untreated hair shafts is measured and a statistical study is performed.

Results/Conclusions:

Following this test, it is found that the application of the peptidic fava bean extract helps in the stimulation of in vitro hair growth. The effect of the extract of the invention is dose-dependent, since better results are obtained with the extract at 1% than with the extract at 0.5%. The best hair-lengthening result is obtained after 7 days of application. By means of the analysis software, a statistical measurement of hair growth was achieved. After 7 days of treatment, hair growth is promoted by more than 219% in the biopsies treated with the active ingredient at 0.5%. The growth is promoted by the order of 234% under condition 2, i.e. with the active ingredient used at 1% (thus showing a dose-dependent effect). It can therefore be concluded that the active ingredient according to the invention has stimulated the growth of hair shafts in vitro.

EXAMPLE 6

Effect of a Peptidic Fava Bean Extract and a Peptidic Corn Extract on Human Dermal Papilla Cell Activity Human dermal papilla cells (HDPC) are maintained in a culture in order to carry out immunostaining of the cell proliferation marker Ki67, a marker associated with the anagen phase of the hair follicle. HDPC cells were chosen since it is from these cells that growth of the hair follicle takes place. The cells are cultured in the presence or absence of the peptidic fava bean extract diluted to 0.5% and a peptidic corn extract at 0.5%, for 48 hours. Untreated controls or controls treated with a single extract are prepared in parallel. After the cells have been washed with PBS, fixed with cold methanol and then rinsed with PBS, the cells are permeabilized with 0.2% Triton X-100 for 15 minutes under stirring. After rinsing with PBS, the primary antibodies are applied. Staining is achieved by means of an anti-Ki67 antibody (Novocastra, mouse monoclonal) diluted to 1/100. After stirring for 60 minutes and rinsing with several PBS baths, 150 μl of a fluorescence-stained secondary antibody diluted to 1/1000 (Invitrogen, Alexa Fluoro 488 anti-mouse) is added and left for 1 hour in darkness under stirring in a humid chamber. Finally, the slides are rinsed in PBS, and mounted between a slide and coverslip with Fluromount G. The fluorescence intensity is quantified by image analysis using the Image-Pro Analyzer software version 5.

Results:

Cells treated with the fava bean extract at 0.5% and cells treated the with the corn extract at 0.5% were respectively 15.5% and 12.8% more stained by the Ki67 antibody than untreated cells. The cells treated with the association of fava bean extract at 0.5%+corn extract at 0.5% demonstrated an even greater Ki67 staining increase (23%).

Conclusion:

The results show that the combination of the fava bean extract of the invention with a peptidic corn extract has a stronger effect on the renewal of human dermal papilla cells.

EXAMPLE 7

Preparation of Compositions

1. Hair Growth Serum

Disperse the Natrosol 250HHR and Disodium EDTA in water under stirring. Heat to 50-60° C., and stir until a uniform appearance is obtained. Add Styleze® CC-10, and stir until a uniform appearance is obtained. Cool to room temperature and add the ingredients in the order listed while stirring until a uniform appearance is obtained between each.

| Formulations INCI Name | Trade Name | No 1 Mass % | No 2 Mass % | Provider |
|---|---|---|---|---|
| Water | | Q.S. | Q.S. | |
| Hydroxyethylcellulose | Natrosol 250HHR | 0.35 | 0.50 | Hercules/Aqualon |
| Disodium EDTA | Dissolvine NA-2S | 0.05 | 0.05 | Akzo Nobel |
| VP/DMAPA Acrylate Copolymers | Styleze ® CC-10 | 5.00 | 5.00 | ISP |
| Quaternium-26 | Ceraphyl ® 65 | 1.00 | 1.00 | ISP |
| Panthenol | Ritapan DL | 0.15 | 0.15 | RITA |
| Propylene Glycol | Liquid | 0.50 | 0.50 | ISP |
| Diazolidinyl urea Iodopropynyl Butylcarbamate | Germall® Plus | | | |
| Peptidic fava bean extract | | 1.00 | 1.00 | ISP |
| Total | | 100.00 | 100.00 | |

Apply to the moistened scalp. Massage to evenly distribute the product. The serum promotes hair growth and/or regrowth while providing it with a firmer appearance.

2. Anti Hair Loss Milk

Pour the water in a suitable vessel and begin stirring. Add Gafquat 755N and Liquid Germall Plus and mix until a uniform appearance is obtained. Add RapiThix A-60 and mix until a uniform appearance is obtained (approximately 15 minutes). Add the hydrolyzate according to Example 2 and stir until a uniform appearance is obtained. Introduce the product into a non-aerosol spray bottle with a Mark VI WL31 Calmar pump.

| Formulations INCI Name | Trade Name | No 1 Mass % | No 2 Mass % | Provider |
|---|---|---|---|---|
| De-ionized water | — | Q.S. | Q.S. | |
| Polyquaternium-11 | Gafquat ® 755N | 1.25 | 2.00 | ISP |
| Propylene Glycol Diazolidinyl urea Iodopropynyl Butylcarbamate/ | Liquid Germall ® Plus | 0.50 | 0.50 | ISP |
| Hydrogenated Sodium Polyacrylate Polydecene Trideceth-6/ | RapiThix ™ A-60 | 0.50 | 0.50 | ISP |
| Peptidic fava bean extract | | 0.1 | 0.5 | ISP |
| | Total | 100.00 | 100.00 | |

The product is adapted for spraying onto the moist scalp and wet hair. Massage to evenly distribute the product. The thus proposed milk helps fight against hair loss, whilst making the hair smoother and easier to style.

The invention claimed is:

1. A method of reducing hair-loss or stimulating hair growth in a subject in need thereof comprising administering a composition comprising an effective amount of a peptidic extract from fava (*Vicia faba* L) beans to an area having hair follicles of said subject, wherein said peptidic extract is obtained by:
    extracting fava beans in an alkaline solution containing polyvinylpolyrrolidone (PVPP) to obtain a crude solution;
    hydrolyzing the crude solution either chemically or with proteolytic enzymes to obtain a hydrosylate;
    solubilizing the hydrolysate in one or more physiologically acceptable solvents;
    filtering the solubilized hydrolysate to obtain a purified peptidic extract comprising at least 70% of peptides having a molecular weight less than 6 kDa;
    wherein said peptidic extract is effective to reduce hair loss or stimulate hair growth.

2. The method of claim 1, wherein the composition stimulates hair growth in cases of age-related hair loss.

3. The method of claim 1, wherein the peptidic extract stimulates the expression of the Ki67 protein and K15 and K14 keratins.

4. The method of claim 1, wherein the peptidic extract is solubilized in one or more physiologically acceptable solvents selected from the group consisting of water, glycerol, ethanol, propylene glycol, butylene glycol, dipropylene glycol, ethoxylated or propoxylated diglycols, cyclic polyols, and any mixture of these solvents.

5. The method of claim 4, wherein the solubilized extract includes at least between 1 and 4 g/l of peptidic compounds.

6. The method of claim 4, wherein the solubilized extract is 0.001% to 5% of the total weight of the composition.

7. The method of claim 1, wherein the composition further comprises at least one compound selected from vitamins, other peptidic plant extracts, esters of nicotinic acid, trace elements, anti-inflammatory agents, retinoic acid or derivatives thereof, retinol, and 5α-reductase inhibitors.

8. The method of claim 7, wherein the other peptidic plant extracts include an extract from corn.

9. The method of claim 1, wherein the administering step is a daily administration of the composition to an area of the scalp to be treated.

10. The method of claim 1, wherein the administering step is a pretreatment of the area having hair follicles prior to exposure to sunlight, chemicals, or heat sources or prior to brushing hair present in the area having hair follicles.

11. The method of claim 1, wherein the peptidic extract comprises at least 85% peptides of less than 6 kDa in size.

12. The method of claim 4, wherein the solubilized extract is 0.01% to 1% of the total weight of the composition.

13. The method of claim 5, wherein the solubilized extract includes at least between 1.5 and 3.5 g/l of compounds of peptidic nature.

14. The method of claim 1, wherein the peptidic extract stimulates the Clock, Per1 and Bmal1 genes in dermal papilla cells of said subject.

* * * * *